(12) United States Patent
Yamada et al.

(10) Patent No.: US 10,004,870 B2
(45) Date of Patent: Jun. 26, 2018

(54) AEROSOL INHALATOR

(71) Applicant: JAPAN TOBACCO INC., Tokyo (JP)

(72) Inventors: Manabu Yamada, Tokyo (JP); Hiroshi Sasaki, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 399 days.

(21) Appl. No.: 14/144,694

(22) Filed: Dec. 31, 2013

(65) Prior Publication Data

US 2014/0109905 A1    Apr. 24, 2014

Related U.S. Application Data

(63) Continuation of application No. PCT/JP2011/068783, filed on Aug. 19, 2011.

(51) Int. Cl.
*H05B 3/00* (2006.01)
*A61M 16/10* (2006.01)
*A61M 15/06* (2006.01)
*A61M 11/04* (2006.01)
*A24F 47/00* (2006.01)
*A61M 16/14* (2006.01)

(52) U.S. Cl.
CPC ....... *A61M 16/1075* (2013.01); *A24F 47/008* (2013.01); *A61M 11/041* (2013.01); *A61M 11/042* (2014.02); *A61M 15/06* (2013.01); *A61M 16/14* (2013.01); *A61M 2205/3368* (2013.01); *A61M 2205/3653* (2013.01); *A61M 2205/8206* (2013.01)

(58) Field of Classification Search
CPC ........ H05B 2203/009; H05B 2203/011; H05B 2203/013; H05B 2203/018; A24F 47/008; A61M 11/041; A61M 11/042; A61M 15/06; A61M 16/1075; A61M 16/14; A61M 2205/3368; A61M 2205/8206
See application file for complete search history.

(56) References Cited

U.S. PATENT DOCUMENTS 3,809,374 A * 5/1974 Schossow ................ F24F 6/18
                                                    261/130
5,666,977 A * 9/1997 Higgins ................ A24F 47/008
                                                  128/200.14
6,155,268 A * 12/2000 Takeuchi ............. A24F 47/008
                                                    131/194

(Continued)

FOREIGN PATENT DOCUMENTS

JP        11-89551 A       4/1999
JP        3325028 B2       9/2002

(Continued)

*Primary Examiner* — Kari Rodriquez
*Assistant Examiner* — Victoria Murphy
(74) *Attorney, Agent, or Firm* — Birch, Stewart, Kolasch & Birch, LLP

(57) ABSTRACT

An aerosol inhalator containing has an inner tube forming part of a suction path, a capillary tube extending within the inner tube and configured to discharge a solution therefrom in conjunction with a user's inhalation, and a heater extending in a direction perpendicular to the axis of the inner tube so as to traverse the inner tube and configured to receive the solution discharged from the capillary tube, wherein the heater atomizes the received solution by heating to generate, inside the inner tube, an aerosol to be inhaled by the user.

13 Claims, 7 Drawing Sheets

(56) References Cited

U.S. PATENT DOCUMENTS

Figure 1:
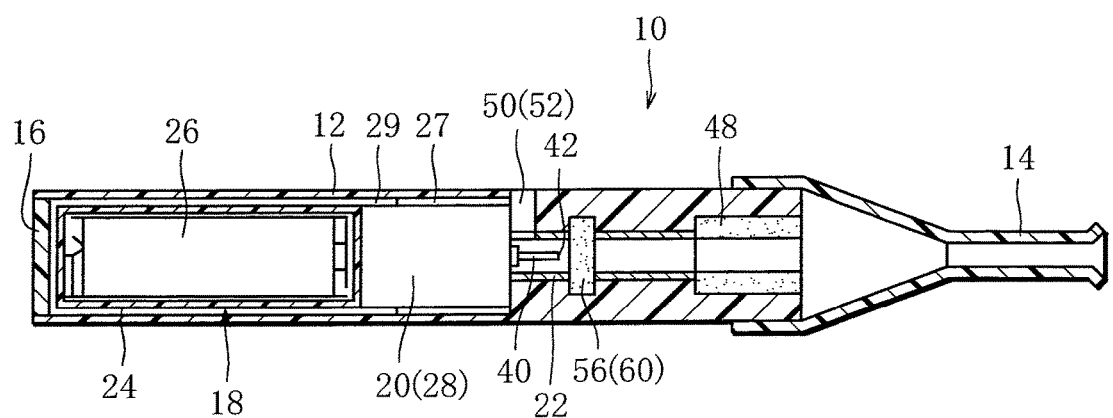
Figure 2:
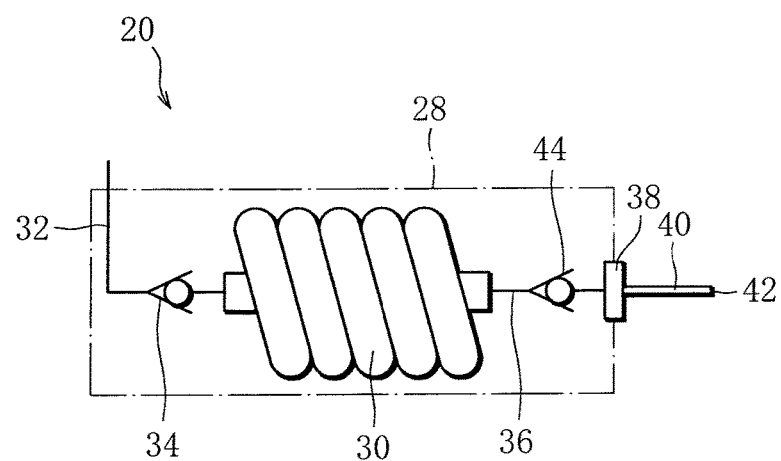

| | | | |
|---|---|---|---|
| 7,537,009 B2* | 5/2009 | Hale | A61K 9/007 |
| | | | 128/200.14 |
| 2001/0003336 A1* | 6/2001 | Abbott | F27D 11/02 |
| | | | 219/543 |
| 2009/0133691 A1 | 5/2009 | Yamada et al. | |
| 2010/0083956 A1* | 4/2010 | Fukumoto | A61M 15/0085 |
| | | | 128/200.14 |
| 2013/0276804 A1 | 10/2013 | Hon | |

FOREIGN PATENT DOCUMENTS

| | | |
|---|---|---|
| JP | 2006-524494 A | 11/2006 |
| JP | 2009-131367 A | 6/2009 |
| WO | WO 97/48293 A1 | 12/1997 |
| WO | WO 2004/095955 A1 | 11/2004 |
| WO | WO 2008/015918 A1 | 2/2008 |

\* cited by examiner

AEROSOL INHALATOR

CROSS REFERENCE TO RELATED APPLICATIONS

Pursuant to 35 USC 120, the present nonprovisional application is the Continuation of PCT/JP2011/068783 filed on Aug. 19, 2011. The entire contents of the above application is hereby incorporated by reference.

TECHNICAL FIELD

The present invention relates to an aerosol inhalator capable of generating an aerosol as a user inhales, to supply the user with the generated aerosol.

BACKGROUND ART

This type of aerosol inhalator is disclosed, for example, in Patent Documents 1 to 4 identified below.

The aerosol inhalator disclosed in Patent Document 1 includes a suction pipe provided with a mouthpiece, a solution supply source incorporated into the suction pipe and storing a solution to be aerosolized, a dispenser capable of supplying a fixed amount of the solution at a time from the solution supply source to a dispensing position within the suction pipe, and an electric heater for heating and thereby atomizing the solution supplied to the dispensing position, to generate an aerosol inside the suction pipe.

The aerosol inhalator disclosed in Patent Document 2 includes an electric heater and a high-frequency generator, in order to aerosolize a liquid fed by a pump.

The aerosol inhalator disclosed in Patent Document 3 includes an ink jet unit for aerosolizing a liquid.

The aerosol inhalator disclosed in Patent Document 4 includes a liquid supply path utilizing capillarity, and an electric heater arranged at the outlet of the liquid supply path.

CITATION LIST

Patent Literature

Patent Document 1: PCT International Publication No. WO 2008/105918 A1
Patent Document 2: PCT International Application-Japanese Translation No. JP 2006-524494 A
Patent Document 3: PCT International Application-Japanese Domestic Re-publication No. WO 97/48293
Patent Document 4: Unexamined Japanese Patent Publication No. JP H11(1999)-89551

SUMMARY OF INVENTION

Technical Problem

The aerosol inhalator of Patent Document 1 requires that the user manually operate the dispenser before inhaling through the mouthpiece, or that the dispenser automatically operate simultaneously with the user's inhalation. The use of the dispenser directly leads to increase in the size of the aerosol inhalator, and also the need for manual operation of the dispenser is a hindrance to the user's easy inhalation of the aerosol.

Automatic operation of the dispenser enables the user to inhale the aerosol with ease, but in this case, the dispenser not only requires a complicated structure but consumes electrical energy for the automatic operation. Consequently, a high-capacity power supply is indispensable for the dispenser and the electric heater, resulting in further increase in the size of the aerosol inhalator.

In the case of the aerosol inhalators of Patent Documents 2 and 3, it is difficult to reduce the sizes of the aerosol inhalators because of their complicated structures, like the aerosol inhalator of Patent Document 1. The aerosol inhalator of Patent Document 4, on the other hand, has a simple structure, compared with the aerosol inhalators of Patent Documents 1 to 3. However, like the aerosol inhalators of Patent Documents 1 to 3, the liquid is aerosolized not by causing the liquid to collide directly with the electric heater, and thus reliable aerosolization is not guaranteed.

An object of the present invention is to provide a small-sized aerosol inhalator which enables a user to inhale an aerosol with ease and also guarantees reliable aerosolization of liquid.

Solution to Problem

The above object is achieved by an aerosol inhalator of the present invention, which comprises:

a suction path connecting an atmosphere-exposed opening and a mouthpiece to each other and permitting air to flow from the atmosphere-exposed opening toward the mouthpiece;

a solution supply device configured to supply a solution from which an aerosol is to be generated, the solution supply device including
a solution supply source storing the solution, and
a capillary tube connected to the solution supply source and having a discharge end located in the suction path and opening in a direction toward the mouthpiece, the capillary tube guiding the solution from the solution supply source to the discharge end and, when the flow of air is produced within the suction path, allowing the solution to be discharged from the discharge end; and a heater device configured to receive the solution discharged from the discharge end and atomize the received solution by heating, the heater device including
a power supply, and
an electric heater arranged immediately downstream of the discharge end and facing the discharge end at a predetermined distance from the discharge end while permitting the flow of air, the heater being configured to generate heat when applied with a voltage from the power supply.

With the above aerosol inhalator, when the user inhales through the mouthpiece, the solution is discharged from the discharge end of the capillary tube. The discharged solution is received on the outer surface of the heater and at the same time is atomized in its entirety by heat generated by the heater, so that an aerosol is generated inside the suction path. The user can therefore inhale the aerosol through the mouthpiece.

Specifically, the heater extends in a direction perpendicular to an axis of the suction path and traverses the suction path. Preferably, the capillary tube extends coaxially with the suction path.

Advantageous Effects of Invention

In the aerosol inhalator of the present invention, the solution is discharged from the discharge end of the capillary tube in conjunction with the user's inhalation, and the discharged solution is received on the outer surface of the heater, so that a total amount of the discharged solution can be atomized on the outer surface of the heater, generating an aerosol inside the suction path. Accordingly, the user can easily and effectively inhale the aerosol.

Details and other advantages of the aerosol inhalator of the present invention will become apparent from the following description when taken in conjunction with the accompanying drawings.

BRIEF DESCRIPTION OF DRAWINGS

FIG. 1 is a schematic longitudinal sectional view of an aerosol inhalator according to one embodiment of the present invention.

FIG. 2 illustrates a specific example of a liquid tank appearing in FIG. 1.

FIG. 3 is an enlarged sectional view of a heater appearing in FIG. 1.

FIG. 4 illustrates the heater in FIG. 1 along with a power feed circuit.

FIG. 5 schematically illustrates part of the aerosol inhalator in a state before an aerosol is generated.

FIG. 6 schematically illustrates part of the aerosol inhalator in a state in which an aerosol is being generated, as viewed in a longitudinal section of an inner tube taken along a longitudinal section of the heater.

FIG. 7 schematically illustrates part of the aerosol inhalator in a state in which an aerosol is being generated, as viewed in a longitudinal section of the inner tube taken along a cross section of the heater.

FIG. 8 illustrates a malfunction of the aerosol inhalator caused in cases where the distance between a capillary tube and the heater is too long.

FIG. 9 illustrates a malfunction of the aerosol inhalator caused in cases where the distance between the capillary tube and the heater is too short.

FIG. 10 schematically illustrates a heating test apparatus for determining an optimum heater.

FIG. 11 is a graph showing measurement results obtained by the heating test apparatus.

FIG. 12 illustrates a modification of a sheath element.

DESCRIPTION OF EMBODIMENTS

As illustrated in FIG. 1, an aerosol inhalator 10 according to one embodiment includes a cylindrical outer tube 12 opening at both ends, and a mouthpiece 14 detachably connected to a proximal end of the outer tube 12. The outer tube 12 and the mouthpiece 14 are each made of heat-resistant synthetic resin. The outer tube 12 has a lid 16 located at its distal end, and the lid 16 is detachable from the outer tube 12.

The outer tube 12 contains a power supply unit 18 as a source of electricity, a liquid tank 20 as a solution supply source, and an inner tube 22. The power supply unit 18, the liquid tank 20 and the inner tube 22 are arranged sequentially in the mentioned order from the lid side coaxially with the outer tube 12. The inner tube 22 communicates with the mouthpiece 14.

The power supply unit 18 and the liquid tank 20 are each replaceable, and with the lid 16 detached from the outer tube 12, the power supply unit 18 and the liquid tank 20 are replaced with new ones.

The power supply unit 18 includes a cell holder 24 and a commercially available battery cell, for example, an AA size cell 26, held by the cell holder 24. The cell 26 has a nominal voltage of 1.5 V and is arranged coaxially with the outer tube 12.

The liquid tank 20 is illustrated in detail in FIG. 2.

The liquid tank 20 includes a cylindrical tank casing 28. The tank casing 28 has a plurality of ribs formed on an outer peripheral surface thereof. The ribs are spaced from each other in a circumferential direction of the tank casing 28 and extend in an axial direction of the tank casing 28 except an end portion of the casing 28 close to the power supply unit 18.

The ribs serve to form a plurality of axial passages 27 (see FIG. 1) between the outer surface of the tank casing 28 and an inner surface of the outer tube 12, and also serve to secure an annular chamber 29 (see FIG. 1) between the aforementioned end portion of the tank casing 28 and the inner surface of the outer tube 12. The annular chamber 29 is connected to the axial passages 27.

A tube coil 30 is contained in the tank casing 28. The tube coil 30 extends in the axial direction of the outer tube 12 and has opposite open ends. An inlet conduit 32 extends from one end of the tube coil 30 to the outer surface of the tank casing 28 and opens on the outer surface of the tank casing 28 to be connected to the annular chamber 29. A check valve 34 is arranged in the inlet conduit 32 and opens only in one direction toward the one end of the tube coil 30.

An outlet conduit 36 extends from the other end of the tube coil 30 and is connected to a capillary tube 40 through a joint 38. The capillary tube 40 projects from the tank casing 28 into the aforementioned inner tube 22 and is located coaxially with the inner tube 22. The projecting end of the capillary tube 40 forms a discharge end 42, which opens in a direction toward the mouthpiece 14. Another check valve 44 is arranged in the outlet conduit 36 and opens only in one direction toward the capillary tube 40.

An internal flow channel (inlet conduit 32, tube coil 30 and outlet conduit 36) of the liquid tank 22 and the capillary tube 40 are filled with a solution to be aerosolized, and the solution reaches the discharge end 42 of the capillary tube 40. The solution may contain, for example, propylene glycol, glycerin or the like.

As is clear from FIG. 1, the inner tube 22 extends from the liquid tank 20 toward the mouthpiece 14 and is connected to an absorbent sleeve 48. The absorbent sleeve 48 is located in alignment with the inner tube 22 and has an inner diameter identical with that of the inner tube 22. A portion of the outer tube 12 surrounding the inner tube 22 and the absorbent sleeve 48 has a larger thickness than a portion of the outer tube 12 surrounding the power supply unit 18 and the liquid tank 20.

Specifically, the inner tube 22 is made of stainless steel or ceramic, for example. On the other hand, the absorbent sleeve 48 is, for example, a paper tube or hollow tubular paper filter capable of absorbing the solution. The absorbent sleeve 48 has a volume sufficient to retain a required absorption amount of the solution.

As illustrated in FIG. 1, the outer tube 12 has a plurality of atmospheric ports 50 formed therein. The atmospheric ports 50 adjoin the liquid tank 20, for example, and are spaced from each other in the circumferential direction of the outer tube 12. Each of the atmospheric ports 50 extends from the outer peripheral surface of the outer tube 12 and penetrates through the inner tube 22. Thus, the atmospheric ports 50 provide atmosphere-exposed openings 52 that open on the outer peripheral surface of the outer tube 12, and are connected to the annular chamber 29 through the axial passages 27.

Accordingly, the atmospheric ports 50 and the inner tube 22 form a suction path connecting the atmosphere-exposed openings 52 to the mouthpiece 14. Also, the atmospheric ports 50 serve to keep the interior of the annular chamber 29 at atmospheric pressure, and as a consequence, the solution in the liquid tank 20 remains in a state such that the solution is always acted upon by the atmospheric pressure through the open end of the inlet conduit 32.

When the user inhales the air in the inner tube 22 through the mouthpiece 14, a negative pressure is created in the inner tube 22, so that ambient air is introduced into the inner tube 22 through the atmospheric ports 50. Such introduction of the ambient air produces, within the suction path, a flow of air toward the mouthpiece 14.

The negative pressure created in the inner tube 22 causes the solution to be discharged from the discharge end 42 of the capillary tube 40 into the suction path, namely, into the inner tube 22, and the amount of the solution discharged is determined by the intensity of the negative pressure. On the other hand, the capillary tube 40 is replenished with the solution from the liquid tank 20 in an amount corresponding to the discharge amount. Since the solution in the liquid tank 20 is always applied with the atmospheric pressure as stated above, the solution in the internal flow channel of the liquid tank 20 moves toward the capillary tube 40 accompanying the replenishment of the solution.

A cylindrical heater 56 is arranged in the inner tube 22. The heater 56 is located immediately downstream of the discharge end 42 of the capillary tube 40, as viewed in the direction of the flow of air produced in the suction path.

Figure 3:
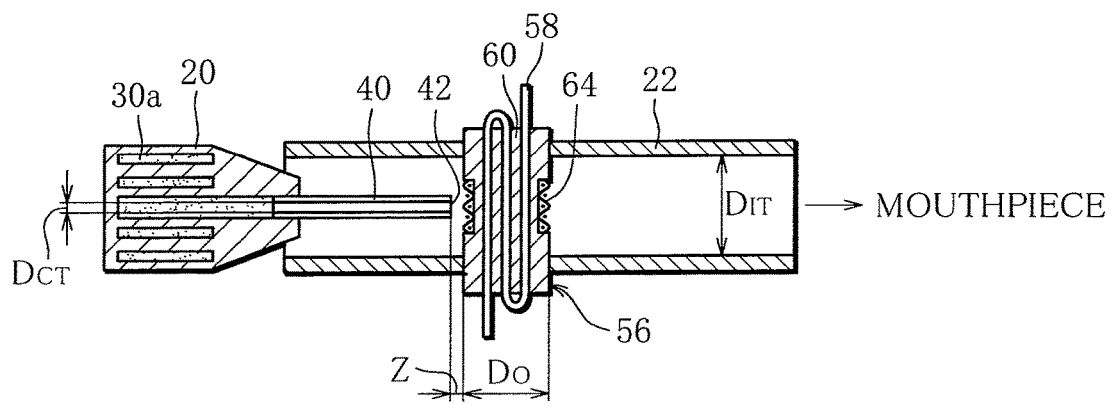

Provided that as shown in FIG. 3, the inner diameters of the inner tube 22 and capillary tube 40 are $D_{IT}$ and $D_{CT}$, respectively, the outer diameter $D_O$ of the heater 56 is smaller than the inner diameter $D_{IT}$ of the inner tube 22 and at the same time is larger than the inner diameter $D_{CT}$ or outer diameter of the capillary tube 40.

That is, the outer diameter $D_O$ satisfies the following relationship:

$$D_{IT} > D_O > D_{CT} \qquad (1)$$

The heater 56 penetrates through the inner tube 22 in a diametrical direction of the tube 22 and has an axis intersecting perpendicularly with the axis of the inner tube 22. The heater 56 is supported at both ends by the outer tube 12.

Considering that the capillary tube 40 is located coaxially with the inner tube 22 as stated above, the discharge end 42 of the capillary tube 40 is hidden by the heater 56 when the heater 56 is viewed from the downstream end of the inner tube 22. In other words, the cross section of the discharge end 42 can be totally projected onto the outer surface of the heater 56.

Further, when the solution is discharged from the discharge end 42 in the aforementioned manner, the discharged solution forms a liquid droplet at the discharge end 42, and a maximum diameter of the liquid droplet is determined by the inner diameter $D_{CT}$ of the capillary tube 40. Provided the maximum diameter of the liquid droplet is $D_{MAX}$, a gap Z between the discharge end 42 and the heater 56 fulfills the following relationship:

$$D_{MAX} > Z > D_{CT} \qquad (2)$$

Thus, when the solution is discharged from the discharge end 42, the discharged solution is received on the outer surface of the heater 56 without fail.

Table 1 below shows the relationship observed where the solution is propylene glycol (PG; density: 1.036 g/mm²), among the discharge amount and volume of the solution discharged in the form of a liquid droplet and the diameter of the liquid droplet with respect to the inner diameter $D_{CT}$ of the capillary tube 40 and the flow rate of intake air flowing through the inner tube 22.

TABLE 1

| | Capillary tube | | | | | |
|---|---|---|---|---|---|---|
| Solution | $D_{CT}$ (mm) | Cross-sectional flow area (mm) | Intake air flow rate | Discharge amount (mg) | Discharge volume (mm³) | Diameter (mm) |
| PG | 0.36 | 0.1 | 35 ml/2 sec | 2.58 | 2.49 | 0.84 |
| | | | 55 ml/2 sec | 3 | 2.90 | 0.88 |
| | 0.5 | 0.2 | 35 ml/2 sec | 5.5 | 5.31 | 1.08 |
| | | | 55 ml/2 sec | 11 | 10.62 | 1.36 |

The liquid tank 20 illustrated in FIG. 3 has a structure different from that of the liquid tank already explained above. Specifically, the liquid tank 20 in FIG. 3 has an internal flow channel 30a extending in a zigzag, in place of the coil tube 30. This means that the coil tube 30 is not indispensable to the liquid tank 20.

The structure of the heater 56 will now be described in detail.

The heater 56 includes, for example, a Nichrome wire 58 as a resistance heating element, and a cylindrical sheath element 60 enclosing the Nichrome wire 58. In this embodiment, as is clear from FIG. 3, the Nichrome wire 58 axially penetrates through the sheath element 60 three times and has two ends projecting from the respective opposite ends of the sheath element 60.

Figure 4:
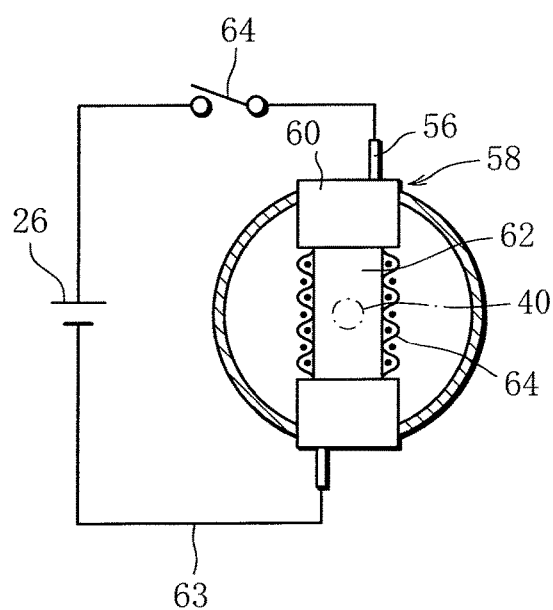

As illustrated in FIG. 4, the Nichrome wire 58 is connected in series with the aforementioned cell 26 via a power feed circuit 63, and the power feed circuit 63 has a switch 64. Although not illustrated in FIG. 1, the power feed circuit 63 and the switch 64 are arranged on the inner surface of the outer tube 12, and the outer tube 12 is provided, on its outer surface, with a push button (not shown) for operating the switch 64.

The sheath element 60 is made of a ceramic such as alumina or silicon nitride, and constitutes the outer surface of the heater 56. Further, as is clear from FIG. 4, an annular groove 62, for example, is formed in part of the outer surface of the sheath element 60, and a ring-shaped heat-resistant net 64, which serves as a wetting enhancement element, is preferably fitted around the annular groove 62. The net 64 directly faces the discharge end 42 of the capillary tube 40, and the aforementioned gap Z is secured between the discharge end 42 and the net 64.

The sheath element 60 not only protects the Nichrome wire 58 but thermally connects the Nichrome wire 58 and the net 64. Specifically, where the cell 26 is in a usable state and the Nichrome wire 58 is applied with a voltage of 1 to 1.5 V, the sheath element 60 performs the function of quickly transferring heat generated by the Nichrome wire 58 to the outer surface of the heater 56 and keeping the heating temperature of the outer surface of the heater 56 within a temperature range required to atomize the solution. That is, the Nichrome wire 58 and the sheath element 60 constitute an internal structure whereby the heating temperature of the outer surface of the heater 56 is kept within the required temperature range, and to this end, the sheath element 60 has a predetermined thickness and volume.

Referring now to FIGS. 5 to 9, the principle of operation of the aerosol inhalator according to the embodiment will be explained. In FIGS. 5 to 9, the net 64 of the heater 56 is not illustrated.

Figure 5:
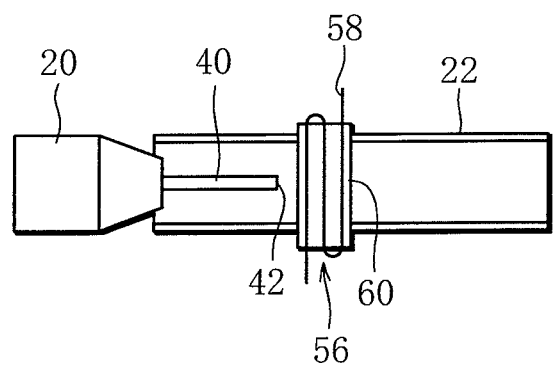
Figure 6:
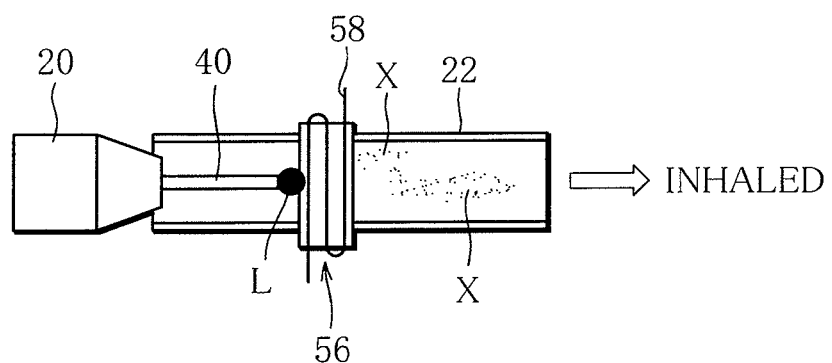
Figure 7:
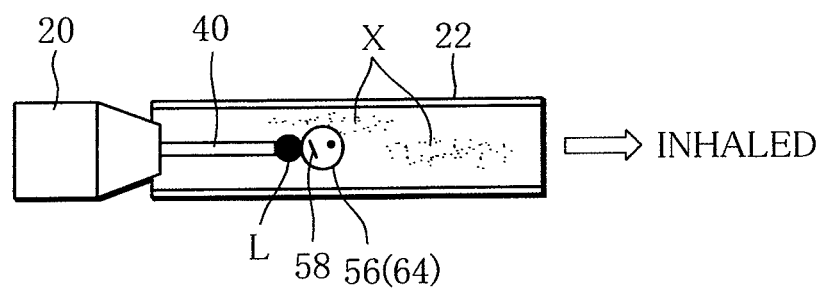
Figure 8:
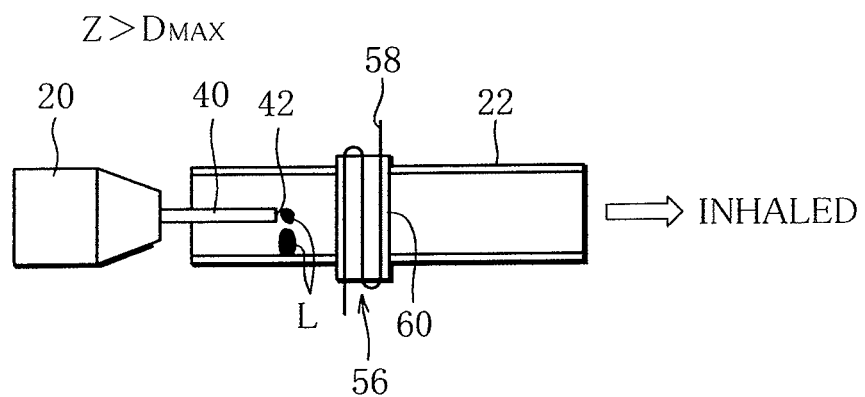
Figure 9:
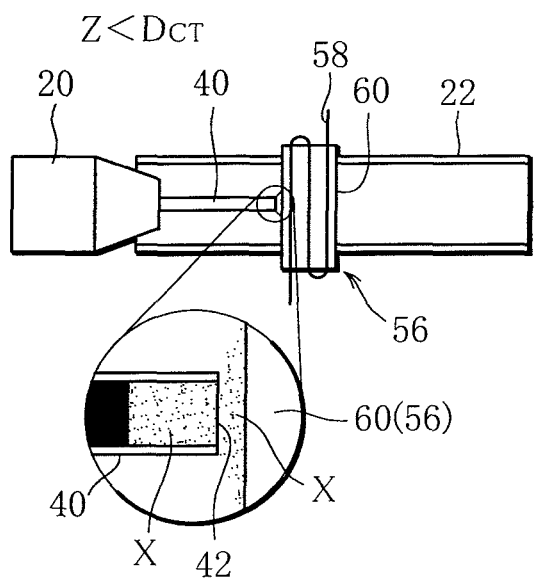
Figure 10:
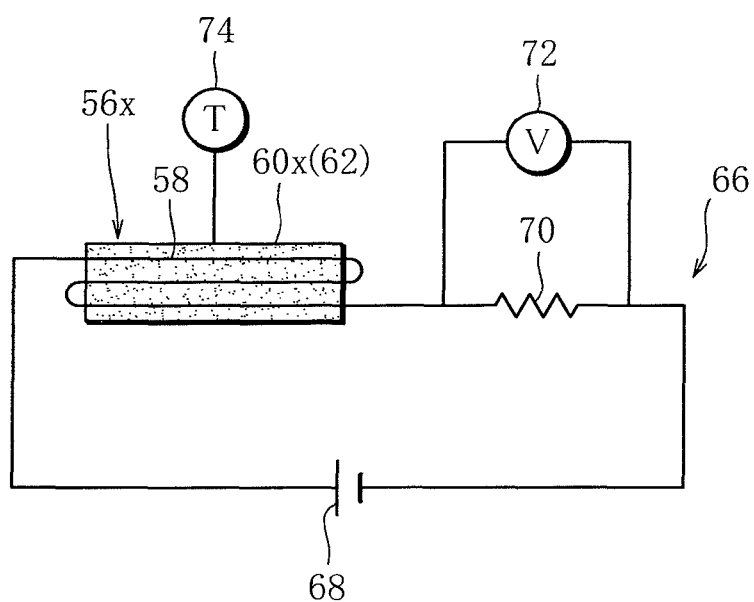

FIG. 5 illustrates a state in which the aerosol inhalator is ready for use with the switch 64 of the power feed circuit 63 turned on. The heating temperature of the outer surface of the heater 56 is quickly raised and kept within the required temperature range, and since the relationship indicated by the aforementioned expression (2) is fulfilled, the solution in the capillary tube 40 is not atomized by the radiant heat from the heater 56. That is, no aerosol is generated.

Figure 11:
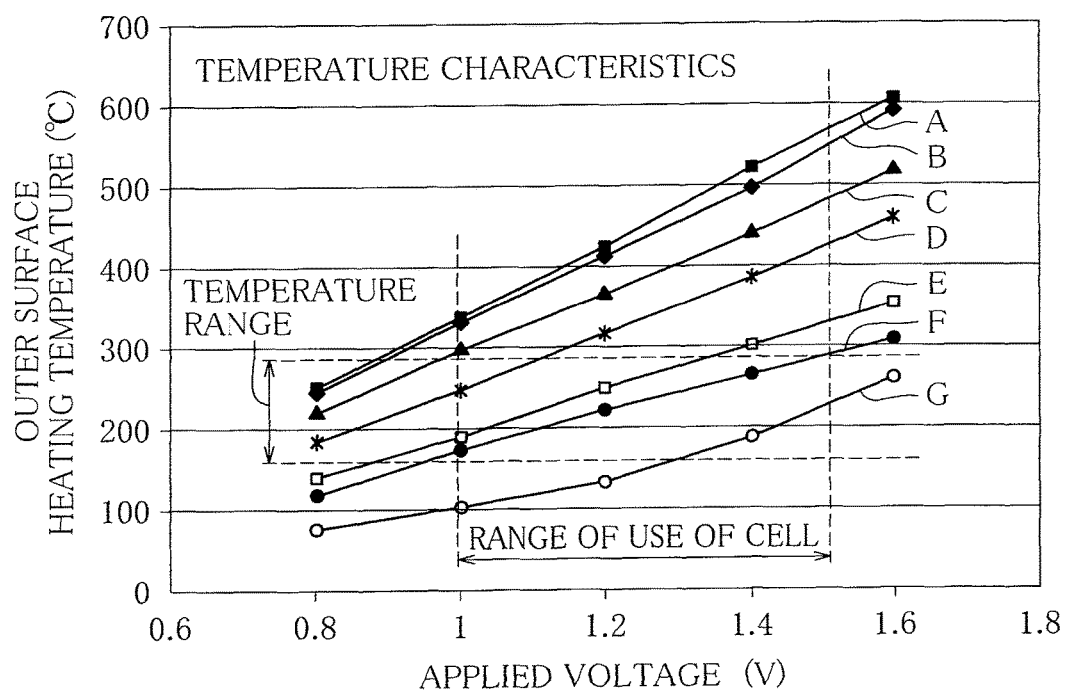

On the other hand, when the user inhales through the mouthpiece 14 of the aerosol inhalator in the state illustrated in FIG. 5, the solution is discharged from the discharge end 42 of the capillary tube 40 as mentioned above. Since the relationships indicated by the expressions (1) and (2) hold between the capillary tube 40 and the heater 56, the discharged solution L is reliably received on the outer surface of the heater 56, as shown in FIGS. 6 and 7. Where the net 64 is fitted around the outer surface of the heater 56, the discharged solution is received by the net 64 and then spreads over the net 64.

At this time, since the heating temperature of the outer surface of the heater 56 is already kept within the required temperature range, the discharged solution L is immediately atomized by being heated by the heater 56, generating an aerosol X inside the inner tube 22. The user can therefore inhale the aerosol X through the mouthpiece 14.

Also, where the heater 56 is provided with the net 64, the net 64 serves to enhance the wettability of the heater 56 with respect to the discharged solution L, so that the discharged solution L can be atomized over a wider area, enabling prompt generation of the aerosol.

As soon as the user ceases breathing in, the discharge of the solution from the discharge end 42 of the capillary tube 40 stops immediately. As is clear from the above explanation, since the gap Z between the discharge end 42 and the outer surface of the heater 56 is greater than at least the inner diameter $D_{CT}$ of the capillary tube 40, the solution in the discharge end 42 is not atomized by the radiant heat from the heater 56 insofar as the heating temperature of the outer surface of the heater 56 is kept within the aforementioned temperature range.

Accordingly, the generation of the aerosol stops at the same time as the cessation of the user's inhalation, so that the solution in the capillary tube 40 is not wasted.

As a result, the user can inhale the aerosol without fail each time he/she breathes in, and the amount of the aerosol inhaled by the user is determined by the intensity and duration of the user's inhalation.

On the other hand, even though the heating temperature of the outer surface of the heater 56 is kept within the required temperature range, the discharged solution L fails to be received on the outer surface of the heater 56 and drops to the inner surface of the inner tube 22, as shown in FIG. 8, if the relationship indicated by the aforementioned expression (2) is not fulfilled and the gap Z is greater than the maximum diameter $D_{MAX}$ of the liquid droplet of the solution. In such a case, the discharged solution L is not atomized, so that the user cannot inhale the aerosol.

Conversely, if the gap Z is smaller than the inner diameter $D_{CT}$ of the capillary tube 40, the solution in the capillary tube 40 is possibly atomized by the radiant heat from the heater 56, as shown in FIG. 9. In this case, the aerosol X is generated independently of the user's inhalation, with the result that the solution in the liquid tank 20 is wasted.

Thus, in the case of the aerosol inhalator of this embodiment, the discharged solution L fails to be atomized, that is, the aerosol fails to be generated, or waste of the solution is unavoidable unless the relationships indicated by the expressions (1) and (2) are fulfilled and also the heating temperature of the outer surface of the heater 56 is kept within an appropriate temperature range.

Specifically, it is necessary that the relationships indicated by the expressions (1) and (2) be fulfilled and also that, where the solution is propylene glycol, the heating temperature of the outer surface of the heater 56 be kept within a temperature range of 180 to 280° C.

The aerosol inhalator of the embodiment does not include a control circuit for controlling the heat generated by the Nichrome wire 58. Thus, in order to keep the heating temperature of the outer surface of the heater 56 within the above temperature range, the thickness (volume) of the sheath element 60 needs to be properly set.

If the sheath element 60 has a larger thickness, it takes a longer time for heat to transfer from the Nichrome wire 58 to the outer surface of the heater 56 via the sheath element 60, and since the area of the outside surface of the sheath element 60 increases, the amount of heat radiated from the sheath element 60 also increases. Thus, it is thought that the larger the thickness of the sheath element 60, the lower the heating temperature of the outer surface of the heater 56 becomes.

In order to confirm such lowering of the heating temperature of the outer surface of the heater 56, the inventors hereof prepared heaters $\mathbf{56}_A$ to $\mathbf{56}_G$ which differed from one another only in the thickness of the sheath element 60. The sheath elements 60 of the heaters $\mathbf{56}_A$ to $\mathbf{56}_G$ had thicknesses progressively increasing in order of $\mathbf{56}_A$ to $\mathbf{56}_G$ each by a fixed increment.

FIG. 10 illustrates a heating test apparatus for a heater $\mathbf{56}_X$ (X represents any one of A to G).

The heating test apparatus includes a power feed circuit 66 for applying a voltage to the heater $\mathbf{56}_X$, and the power feed circuit 66 includes a direct-current power supply 68 capable of varying the applied voltage, a shunt resistor 70 (1 mΩ), and a voltmeter 72. The heater $\mathbf{56}_X$ is connected in series with the shunt resistor 70.

Further, the heating test apparatus includes a temperature sensor 74, which is capable of measuring the temperature of the heater $\mathbf{56}_X$, that is, the temperature of the outer surface of the sheath element 60. Specifically, the temperature sensor 74 includes a type K thermocouple.

When the heater $\mathbf{56}_X$ is connected to the power feed circuit 66 as illustrated in FIG. 10, a voltage is applied from the direct-current power supply 68 to the Nichrome wire 58 of the heater $\mathbf{56}_X$, so that the Nichrome wire 58 generates heat. The heat generated by the Nichrome wire 58 is transferred through the sheath element 60, thus increasing the temperature of the sheath element 60, and on the other hand is released to the outside from the outer surface of the sheath element 60.

Consequently, the heating temperature of the outer surface of the sheath element 60 is determined by a difference between the amount of heat generated by the Nichrome wire 58 and the amount of heat released from the sheath element 60, and the rate of temperature increase of the outer surface of the sheath element 60 is determined by the rate of heat transfer through the sheath element 60.

A heating test was conducted on the heater $\mathbf{56}_X$ in such a manner that with the applied voltage, applied to the Nichrome wire 58 from the direct-current power supply 68, sequentially varied within a range of 0.8 V to 1.6 V, the heating temperature of the outer surface of the sheath element 60 was measured by the temperature sensor 74 with respect to each of the applied voltages of the Nichrome wire 58. The measurement results are shown in FIG. 11.

As is clear from FIG. 11, the outer surface of the sheath element 60 of the heater $56_X$ is heated to a higher temperature as the voltage applied to the Nichrome wire 58 increases.

Considering, however, ordinary use of the AA size cell 26 which is expected to apply a voltage of 1.0 V to 1.5 V, the heater $56_F$ alone is capable of keeping the heating temperature of the outer surface of the sheath element 60 within the aforementioned temperature range (180 to 280° C.)

This means that where the heater $56_F$ is used as the heater 56 of the aerosol inhalator 10 of the embodiment, the heating temperature of the outer surface of the heater 56 can be kept within the required temperature range without the need to use a control circuit for controlling the voltage applied to the Nichrome wire 58.

Since the aerosol inhalator 10 need not be provided with such a control circuit, the load on the cell 26 is reduced, whereby the aerosol inhalator 10 can be used for a long period of time. Further, the use of the cell 26 serves to make the aerosol inhalator 10 smaller in size and slenderer, improving handiness of the aerosol inhalator 10.

If, on the other hand, the user inhales in a situation where the heating temperature of the outer surface of the heater 56 is lower than the aforementioned temperature range due to voltage reduction of the cell 26, the solution discharged from the capillary tube 40 may be insufficiently atomized and part of the discharged solution may possibly adhere to the inner surface of the inner tube 22.

Further, it is also conceivable that even though the heating temperature of the outer surface of the heater 56 is kept within the aforementioned temperature range, the generated aerosol condenses on the inner surface of the inner tube 22, with the result that the solution adheres to the inner surface of the inner tube 22.

In such cases, as the user inhales, the adherent solution may move toward the mouthpiece 14 and possibly flow into the user's mouth.

However, since the absorbent sleeve 48, which is a paper tube or paper filter, is arranged between the inner tube 22 and the mouthpiece 14, the adherent solution, if moved toward the mouthpiece 14, is reliably absorbed into the absorbent sleeve 48 and does not flow into the user's mouth.

The present invention is not limited to the aerosol inhalator 10 of the foregoing embodiment and may be modified in various ways.

As regards the heater 56, for example, the resistance heating element is not limited to Nichrome wire, and the cross-sectional shape of the heater 56 is not limited to circle and may instead be ellipse, polygon or the like.

Figure 12:
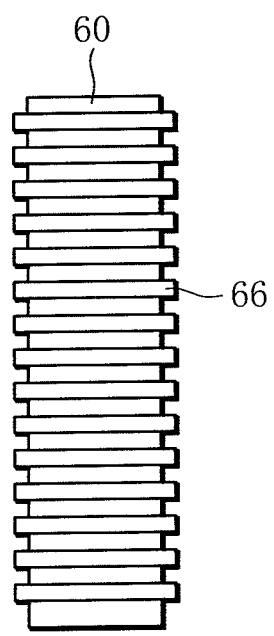

The sheath element 60 may be made of metal and, as shown in FIG. 12 by way of example, may have a rough outer surface 66 formed on at least a portion thereof where to receive the discharged solution, in place of the aforementioned net 64. The rough outer surface 66 is constituted, for example, by a large number of narrow annular grooves spaced from each other in the axial direction of the sheath element 60, and when the discharged solution is received on the outer surface 66 of the sheath element 60, the annular grooves serve to spread the discharged solution, like the net 64.

Further, where the sheath element 60 of the heater 56 and the inner tube 22 are to be made of the same ceramic, the sheath element 60 and the inner tube 22 are preferably formed as a one-piece molded article, and in this case, the number of parts of the aerosol inhalator can be reduced.

REFERENCE SIGNS LIST

12: outer tube
14: mouthpiece
18: power supply unit
20: liquid tank
22: inner tube
26: cell
40: capillary tube
42: discharge end
48: absorbent sleeve (paper tube, paper filter)
50: atmospheric port
52: atmosphere-exposed opening
56: heater
58: Nichrome wire (resistance heating element)
60: sheath element
64: net (wetting enhancement element)

The invention claimed is:

1. An aerosol inhalator comprising:
a suction path connecting an atmosphere-exposed opening and a mouthpiece to each other and permitting air to flow from the atmosphere-exposed opening toward the mouthpiece;
a solution supply device configured to supply a solution from which an aerosol is to be generated, said solution supply device including
a solution supply source storing the solution, and
a capillary tube which extends coaxially with the mouthpiece, and
a discharge end of the capillary tube having
an opening in a direction toward the mouthpiece and discharging the solution from the solution supply source when the flow of air is produced within said suction path; and
a heater device configured to receive the solution discharged from the discharge end and to atomize the received solution by heating, said heater device including
a power supply, and
an electric heater arranged facing the discharge end so that a gap having a predetermined distance and extending along the suction path in a direction that is parallel to a longitudinal axis of the aerosol inhalator is provided between the discharge end and the electric heater, the electric heater being configured to generate heat when applied with a voltage from the power supply, wherein the discharge end of the solution supply device is arranged in a position such that a cross section of the discharge end is disposed perpendicular to said longitudinal axis, whereby the discharge end is totally projected onto a surface of the electric heater, wherein the predetermined distance is longer than a diameter of the opening of the discharge end.

2. The aerosol inhalator according to claim 1, wherein the heater extends in a direction perpendicular to an axis of said suction path.

3. The aerosol inhalator according to claim 1, wherein the electric heater has a cylindrical shape and the opening of the discharge end has a diameter smaller than that of the heater.

4. The aerosol inhalator according to claim 1, wherein the electric heater has a non-smooth region on at least part of an outer surface thereof and receives the discharged solution on the non-smooth region.

5. The aerosol inhalator according to claim 1, wherein the electric heater includes an internal structure which is configured to maintain the heating temperature of an outer surface of the electric heater within a predetermined temperature range required to atomize the discharged solution, by using only the applied voltage and heat radiated from the outer surface of the heater.

6. The aerosol inhalator according to claim 1, wherein the electric heater includes a textured heating surface for receiving the solution discharged from the discharge end.

7. The aerosol inhalator according to claim 6, wherein the textured heating surface comprises a wetting enhancement element configured to cause the discharged solution received on the textured heating surface of the electric heater to spread over the textured heating surface.

8. The aerosol inhalator according to claim 1, wherein the power supply includes a commercially available battery cell.

9. The aerosol inhalator of claim 1, wherein the heater device includes a non-planar heating surface for receiving the solution discharged from the discharge end of the solution supply source.

10. The aerosol inhalator of claim 1, wherein the predetermined distance is adapted so that a liquid droplet of the solution is formed at the discharge end of the solution supply source by surface tension of the solution and the formed liquid droplet is received by a surface of the electric heater before leaving the discharge end.

11. The aerosol inhalator of claim 1, wherein the solution supply device is configured to discharge the solution in the solution supply source through the opening of the discharge end based on a negative pressure created in the suction path when the air flows toward the mouthpiece.

12. The aerosol inhalator according to claim 1, wherein the heater extends across the suction path and perpendicular to an axis of the discharge end of the solution supply device, whereby a total amount of the discharged solution is atomized on the outer surface of the heater, generating the aerosol inside the suction path.

13. The aerosol inhalator of claim 12, wherein the predetermined distance is adapted so that a liquid droplet of the solution is formed at the discharge end by surface tension of the solution and the formed liquid droplet is received by a surface of the electric heater before leaving the discharge end.

* * * * *